United States Patent [19]
Pick

[11] Patent Number: 6,027,468
[45] Date of Patent: Feb. 22, 2000

[54] WALKING BRACE WITH ENHANCED SHOCK ABSORBENCY

[75] Inventor: Erez Pick, Bayside, N.Y.

[73] Assignee: Aircast, Inc., Summit, N.J.

[21] Appl. No.: 09/040,839

[22] Filed: Mar. 18, 1998

[51] Int. Cl.$^7$ ..................................................... A61F 5/00
[52] U.S. Cl. .................... 602/27; 602/5; 602/23
[58] Field of Search ..................... 602/5, 13, 23, 602/27–29, 2; 128/882, 892; 5/649–651; 36/13, 24.5, 83–90, 110, 113, 140–155, 156–171, 173, 178, 181

[56] References Cited

U.S. PATENT DOCUMENTS

| | | | |
|---|---|---|---|
| 3,633,573 | 1/1972 | Lipson et al. | 128/83.5 |
| 3,955,565 | 5/1976 | Johnson, Jr. . | |
| 5,370,604 | 12/1994 | Bernardoni | 602/27 |
| 5,464,385 | 11/1995 | Grim | 602/27 |
| 5,577,998 | 11/1996 | Johnson, Jr. et al. . | |

OTHER PUBLICATIONS

Dale, P.A. et al., "A New Concept in Fracture Immobilization," *Clinical Orthopaedics and Related Research*, No. 295, pp. 264–269 (1993).

Brochure on Equallizer Air Walker, Royce Medical Company.

Primary Examiner—Richard J. Apley
Assistant Examiner—Jayne Saydah
Attorney, Agent, or Firm—Jones, Day, Reavis & Pogue

[57] ABSTRACT

A walking brace is disclosed having enhanced shock absorbing at the patient's heel. A layer of shock-absorbing material disposed along the bottom of the walking brace has a heel portion that extends upwardly through an opening in the sole portion of the walking brace to engage the patient's heel. The bottom of the patient's heel is never engaged, either directly or indirectly by the rigid plastic of the walking brace sole portion.

6 Claims, 2 Drawing Sheets

WALKING BRACE WITH ENHANCED SHOCK ABSORBENCY

BACKGROUND OF THE INVENTION

1. Field of the Invention

The present invention relates generally to orthopedic devices, and more particularly, to those orthopedic devices known variously as casts, splints, braces, etc., which are specially adapted for immobilizing and/or protecting injured limbs or other parts of the anatomy.

2. Description of the Prior Art

In the management of certain injuries to the lower extremities such as fractures of the tibia and fibula, malleolar fractures, or severe ankle sprains, it is common to immobilize the lower extremity completely by use of the well-known molded plaster or resin cast. Once the injured extremity has become stable, however, it has been found that recovery may be effected more rapidly by gradually and progressively permitting the extremity to bear weight and undergo other permitted exercises.

For example, an orthopedic brace, such as that disclosed in U.S. Pat. No. 3,955,565, which is assigned to the assignee herein and incorporated herein by reference in its entirety, may be used. This brace features one or more rigid outer shell members having associated therewith an inflatable liner or air cell for engaging a body part or limb. Commercial embodiments of the brace incorporating the invention disclosed in this prior patent are adapted to be fixed about the lower leg and typically comprise a rear outer shell member, a front outer shell member, and air cells disposed within the liner of the shell members. Strap fastening means maintain the shell members in engagement with confronting portions of the lower leg whereby each air cell serves as a firm supporting cushion of pressurized air between the irregular contours of the lower leg and the member sidewalls.

This brace construction is capable of stabilizing the ankle and leg while allowing the wearer to walk. Thus, ambulatory functionality and permitted exercises are feasible thereby encouraging more rapid recovery from various injuries to the lower extremity than otherwise would be possible. Moreover, studies have indicated that a pressurized brace yields a stronger fracture than a conventional cast. Dale, P.A. et al., "A New Concept in Fracture immobilization," Clinical Orthopedics and Related Research, 264–269 (1993).

An improved version of an orthopedic walking brace is disclosed in U.S. Pat. No. 5,577,998 also assigned to the assignee herein and incorporated herein by reference in its entirety. This walking brace includes a passive reinflation means disposed within the air cells so that no external equipment or oral inflation tube for reinflation of the air cells is required.

Various types of braces are known for this purpose. All such braces include a leg portion that fits on to the patient's lower leg, and a sole portion that fits beneath the patient's foot. The leg portion can be, for example, a pair of opposing splints connected by foam, although a rigid plastic shell leg portion is preferred. In all such cases, however, the sole portion will be a rigid material to properly support and position the foot with respect to the leg during activity.

The bottom of the sole portion is typically provided with a layer of a highly durable shock-absorbing material to reduce the jarring impact caused by the patient's walking on the injured leg or foot. The upper surface of the sole portion is provided with a soft foam layer to provide a cushion between the patient's foot and the hard upper surface of the sole portion of the rigid exterior shell.

It would be desirable to provide enhanced shock absorbency to walking braces of this type. A need for improved shock absorbency is particularly great in the heel portion of the walking brace which experiences the greatest repeated impact from normal walking. Repeated impact of the heel on a rigid surface can result in a greater than normal load on the heel, which can lead to sores or bruising. This problem can be particularly severe in patients having neuropathy in the foot; since these individuals cannot feel bruises or the initial sores, such sores or bruises can go unchecked and develop into ulcerations. Greater cushioning and shock absorbency can reduce or even prevent such occurrences.

Some prior art devices have attempted to provide shock absorbency in the heel area by means of an extra piece of soft foam material in the vicinity of the heel above the upper surface of the sole portion of the exterior shell and usually below the soft foam layer. Such devices have the disadvantage of further raising the heel of the injured leg relative to the heel of the uninjured leg such that the patient's legs are effectively of two different lengths, thereby making walking even more difficult. Another device of the prior art manufactured by Royce Medical Company under the name "Equalizer Air Walker" tries to address this problem by providing a slot or recess in the anterior portion of the posterior shell at the heel just below the upper surface of the sole portion of the shell and providing an extra piece of shock-absorbing material in that recess. The patient's foot, however, including the patient's heel, is still disposed along the entire rigid upper surface of the sole portion of the exterior shell.

It is thus one object of the invention to provide a walking brace having improved shock absorbency at the patient's heel.

It is another object of the invention to provide a walking brace that provides greater long term comfort to the patient when in use.

It is yet another object of the invention to provide a walking brace having improved shock absorbency at the heel, yet which does not substantially raise the patient's heel above the upper surface of the sole portion of the walking brace.

SUMMARY OF THE INVENTION

The instant invention comprises a walking brace for immobilizing and/or protecting the lower leg of a patient. The brace comprises a leg portion adapted to fit substantially around the lower leg of a patient, and a sole portion that fits beneath the patient's foot. The sole portion comprises an upper surface that engages the sole of the patient's foot and a lower surface that engages the ground when the walking brace is used by the patient for walking or standing. The upper surface of the sole portion is preferably provided with a soft foam layer. The lower surface of the sole portion is preferably provided with a layer of a durable shock-absorbing material.

In accordance with the invention, the sole portion of the walking brace is provided with an opening in the area of the patient's heel and the layer of shock-absorbing material includes a heel portion which extends upwardly through the opening in the sole portion. Thus, when the patient stands or walks using the inventive walking brace, the patient's heel impacts the resilient shock absorbing material of the heel portion of the layer while the rest of the patient's foot engages the rigid upper surface of the sole portion. This reduces load damage to the patient's heel and reduces shock experienced by the patient when using the brace. The invention is particularly useful for those patients having neuropathy in the foot such as may be caused by certain diabetic conditions by reducing ulceration that can be caused by repeated engagement of the patient's heel against a rigid structure.

DETAILED DESCRIPTION OF THE INVENTION

Figure 1:
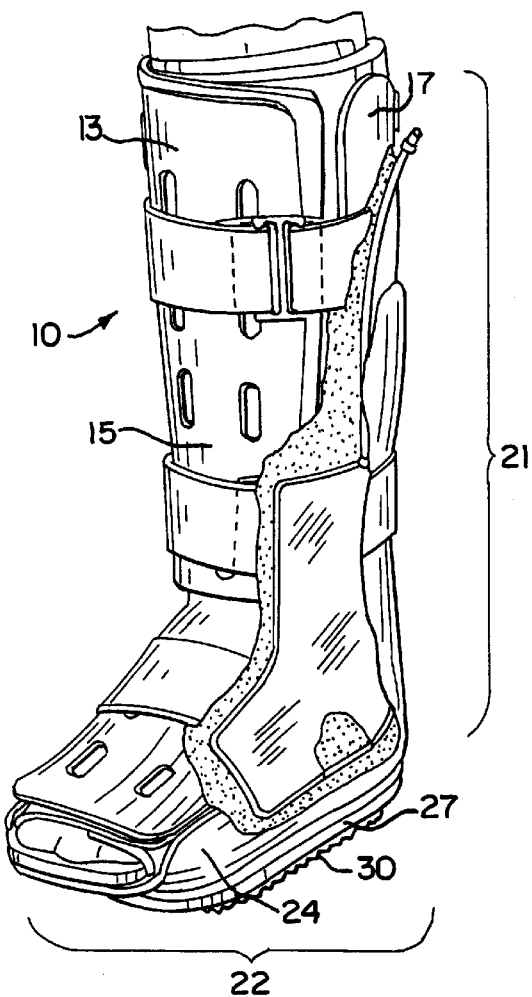
FIG. 1 is a view of the exterior of a prior art walking brace which can be adapted for use with the instant invention.

The invention comprises a walking brace that provides improved shock absorbency to the heel area of the patient. For purposes of illustration, the inventive walking brace will be described herein as the preferred embodiment in which the leg portion is a rigid exterior shell. It will be recognized, however, that the scope of the instant invention is not so limited, and may also be used in walking brace embodiments in which the leg portion is not a rigid shell, such as, for example, those in which the leg portion comprises one or more splints and connecting foam.

Referring to the Figures, a preferred embodiment of the walking brace 10 includes a rigid exterior shell 13 comprising a front shell portion 15 and a rear shell portion 17. It may be seen that exterior shell 13 is adapted to fit substantially around the lower leg and foot of a patient.

The interior surfaces of both the front and rear shell portions 15, 17 are preferably provided with a plurality of inflatable air cells which may be actively or passively inflated as taught in the aforementioned prior art patents, U.S. Pat. No. 3,955,565 and U.S. Pat. No. 5,577,998. The walking brace of the invention can also include one or more pre-inflated cells and one or more foam liner portions to cushion the leg against the shell portions to provide greater comfort. Other arrangements of air cells and liners may be used without departing from the spirit of the invention disclosed and claimed herein. The use of such air cells and liners, however, is not essential to the practice of the instant invention.

Figure 2:
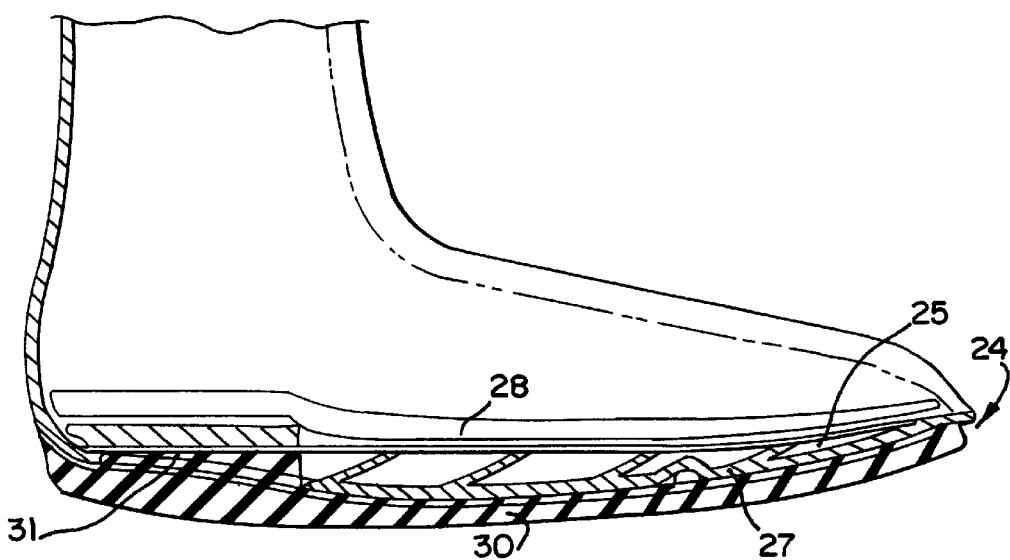
FIG. 2 is a cross-sectional view of the sole portion of a walking brace of the instant invention.
Figure 3:
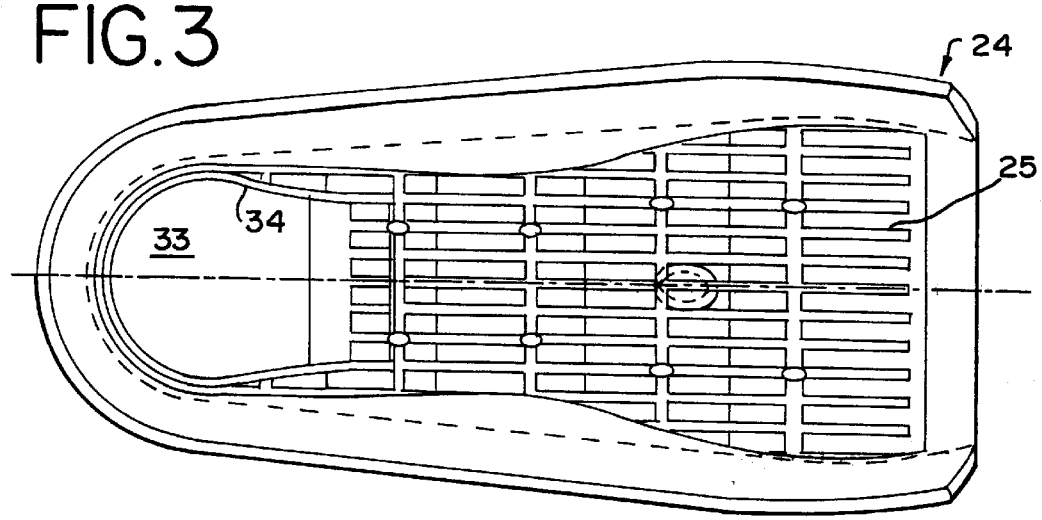
FIG. 3 is a plan view of the upper surface of the sole portion of the walking brace.
Figure 4:
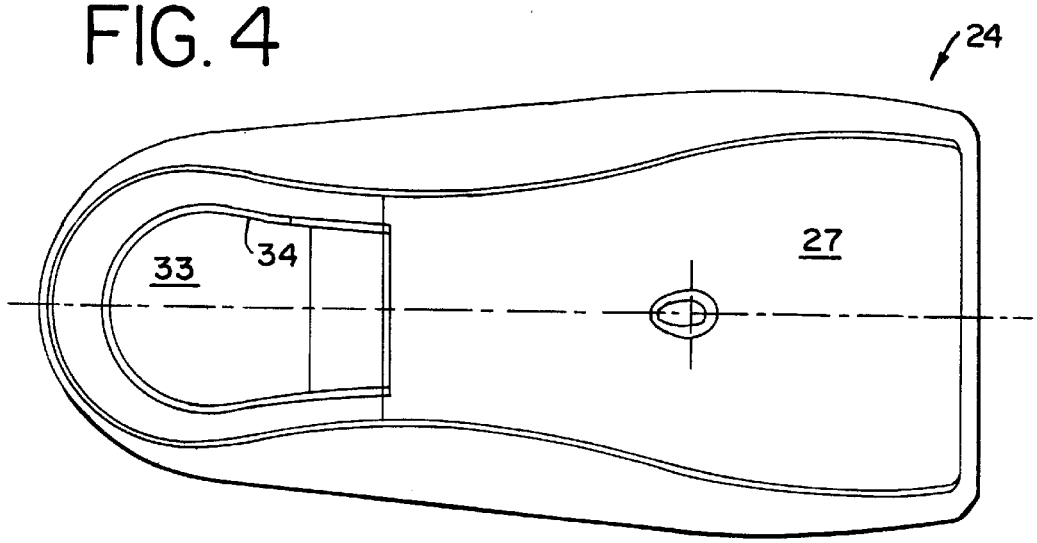
FIG. 4 is a plan view of the bottom surface of the sole portion of the walking brace.
Figure 5:
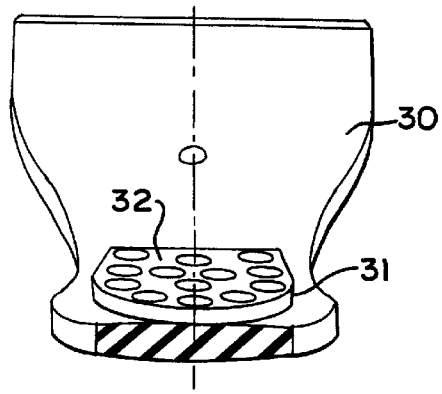
FIG. 5 is a rear perspective view of a layer of shock absorbing material configured to be used in the walking brace of the instant invention.

Rear shell portion 17 of walking brace 10 includes a leg portion 21 adapted to fit around the anterior surface and sides of the patient's lower leg and a foot portion 22 configured to fit around the sides and bottom of the patient's foot. Foot portion 22 includes a sole portion 24 adapted to fit beneath the sole of the patient's foot. Sole portion 24 includes an upper surface 25 and a lower surface 27. As shown most clearly in FIG. 2, upper surface 25 preferably is provided with a foam cushion 28 which preferably extends throughout the length and width of upper surface 25. Lower surface 27 preferably is provided with a layer 30 of a durable shock resistant material.

In accordance with the invention, sole portion 24 of the exterior shell is provided with an opening 33 in the general area of the patient's heel. Opening 33 extends completely through sole portion 24 from lower surface 27 to upper surface 25. Opening 33 is preferably provided with a circumferential ridge 34. Layer 30 includes a heel portion 31 which is of the same shape as opening 33 and is configured to extend upwardly therethrough. Heel portion 31 has an upper surface 32 such that when layer 30 is positioned in engagement with lower surface 27 of sole portion 24, the upper surface 32 of heel portion 31 is generally coplanar with or only slightly above the upper surface 25 of sole portion 24. Upper surface 25 preferably is provided with a foam layer 28 that extends over both upper surface 25 and upper surface 32 of heel portion 31. Optionally, an extra piece of foam 35 can be positioned between heel portion 31 and foam layer 28 to provide additional cushioning to the patient's heel.

While heel portion 31 may be manufactured separately and adhered to shock-absorbing layer 30, it is more expedient from a manufacturing standpoint to provide heel portion 31 and layer 30 as a single integrally molded piece. Heel portion 31 and layer 30 can be made of any resilient, durable, shock-absorbing material. Typical suitable materials include polyvinyl chloride (PVC) and styrene-butadiene rubber (SBR); a particularly preferred material is thermoplastic rubber (TPR). Molding conditions for such materials are known to those skilled in the art.

The walking brace of the instant invention is advantageous in that the patient never exerts weight, either directly or indirectly, through the bottom of the patient's heel against the rigid plastic of the sole portion 24 of the exterior shell. The bottom of the patient's heel only engages the foam cushion and, indirectly, the resilient, shock-absorbing material of heel portion 31 and layer 30. Yet the patient's heel is not raised substantially above upper surface 25 of sole portion 24, so the invention does not unduly affect the mechanics of the patient's walking. The instant invention reduces the load damage on the patient's heel that can be caused with certain devices of the prior art, which is particularly beneficial to those patients having neuropathy in the foot.

While the invention has been shown and described with respect to a particular embodiment, this is for the purpose of illustration rather than limitation. The inventor envisions, and it will be apparent to those skilled in the art, that other variations and modifications of the embodiment shown and described herein are all within the intended spirit and scope of the invention. Accordingly, the patent is not to be limited in scope and effect to the specific embodiment shown and described nor in any other way that is inconsistent with the extent to which the progress and the art has been advanced by the invention.

What is claimed is:

1. A walking brace for the lower leg of a patient, said walking brace comprising:
   a leg portion adapted to fit substantially around the lower leg of a patient,
   a rigid sole portion adapted to fit beneath the foot of a patient, said rigid sole portion having an opening therethrough in the area of the patient's heel said opening extending through said upper surface and said lower surface of said rigid sole portion, such that no portion of said rigid sole portion is disposed below the patient's heel; and a layer of resilient shock-absorbing material disposed along said bottom surface of said rigid sole portion, said layer of resilient shock-absorbing material having continuous a heel portion extending upwardly through said opening in said sole portion to a height no greater than slightly above said upper surface of said rigid sole portion such that in use the patient's heel exerts force against said resilient, shock absorbing heel portion and not against said rigid sole portion, and such that in use the patient's heel is not raised substantially above said upper surface of said rigid sole portion.

2. The walking brace of claim 1 wherein said heel portion is integrally formed with said layer of shock-absorbing material.

3. The walking brace of claim 1 wherein said heel portion has an upper surface substantially coplanar with said upper surface of said sole portion.

4. The walking brace of claim 1 wherein said layer and heel portions are made of a material selected from the group consisting of thermoplastic rubber, polyvinyl chloride, and styrene-butadiene rubber.

5. The walking brace of claim 1 further having a foam layer disposed over the upper surface of said sole portion.

6. The walking brace of claim 1 wherein said leg portion comprises a rigid shell integral with said sole portion.

* * * * *